(12) United States Patent  
Chen et al.

(10) Patent No.: US 8,236,154 B2
(45) Date of Patent: Aug. 7, 2012

(54) COMPOSITE MODIFIED ELECTRODE STRIP

(75) Inventors: Sz-Hau Chen, Hsinchu (TW);
Chih-Sheng Lin, Hsinchu (TW);
Guan-Tin Chen, Hsinchu (TW);
Yueh-Hui Lin, Hsinchu (TW); Thomas Y. S. Shen, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 814 days.

(21) Appl. No.: 12/139,883

(22) Filed: Jun. 16, 2008

(65) Prior Publication Data
US 2009/0008247 A1 Jan. 8, 2009

(30) Foreign Application Priority Data
Jul. 5, 2007 (TW) .............................. 96124501 A

(51) Int. Cl.
*G01N 27/327* (2006.01)
(52) U.S. Cl. .................................. 204/403.14; 204/400
(58) Field of Classification Search .................. 204/400, 204/403.01–403.15; 205/777.5, 778, 792; 600/345–348
See application file for complete search history.

(56) References Cited

U.S. PATENT DOCUMENTS

| 4,545,382 | A | * | 10/1985 | Higgins et al. | ................. | 600/347 |
| 4,945,045 | A | | 7/1990 | Forrest et al. | | |
| 5,837,454 | A | * | 11/1998 | Cozzette et al. | ................. | 435/6 |
| 6,241,863 | B1 | * | 6/2001 | Monbouquette | ........... | 205/777.5 |
| 6,254,736 | B1 | | 7/2001 | Earl et al. | | |
| 6,491,803 | B1 | | 12/2002 | Shen et al. | | |
| 6,923,894 | B2 | | 8/2005 | Huang et al. | | |
| 2005/0133368 | A1 | * | 6/2005 | Davies et al. | ............ | 204/403.01 |

FOREIGN PATENT DOCUMENTS

| CN | 1462880 A | 12/2003 |
| CN | 1462881 A | 12/2003 |
| TW | I252919 | 4/2006 |
| TW | I276799 | 3/2007 |

OTHER PUBLICATIONS

Office Action dated May 20, 2010 for 096124501 which is a corresponding Chinese application that cites US 6491803, and US 4945045, and TW 1252919.

\* cited by examiner

*Primary Examiner* — Alex Noguerola
*Assistant Examiner* — Gurpreet Kaur
(74) *Attorney, Agent, or Firm* — WPAT, P.C.; Anthony King

(57) ABSTRACT

The present invention provides a surface-modified electrode strip for measuring an electrochemical signal that is synergistically amplified by means of a nano-scaled gold particle layer and a lipid-soluble electron mediator layer. A biosensor comprising the electrode strip is also provided.

26 Claims, 6 Drawing Sheets

COMPOSITE MODIFIED ELECTRODE STRIP

FIELD OF THE INVENTION

The present invention relates to the utilization of a nano-scaled gold particle layer and a lipid-soluble electron mediator layer so that the electrochemical signal measured by the electrode strip can be synergistically amplified, and to the biosensor comprising the strip.

BACKGROUND OF THE INVENTION

The biosensory analytical technique has become one of the most important technologies in the $21^{st}$ century. Biosensors are analytical systems that utilize the biosensory analytical technique, and consist of biological identification materials and various signal converters. Among them, an electrochemical biosensor is easy to operate and has outstanding sensitivity, and therefore is an excellent sensory element. In addition, in view of the specificity of different biological molecules, the problem of selectivity in most sensory elements can be overcome. Since a biosensor with an electrode strip, such as an enzymatic-electrochemical sensor, can provide an accurate result rapidly, it is widely used in detecting a large amount of samples in research and clinical studies. For example, the electrochemical blood sugar detecting systems sold in the market use an electrode coated with a glucose oxidase to measure the concentration of the glucose molecule. The development of enzyme-immobilized biosensors generally has three stages. The first stage is the utilization of a dissolved oxygen-detecting electrode in the measurement of the amount of the dissolved oxygen consumed during the catalytic process of the substance with the oxidative enzyme, so that the concentration of the substance can be indirectly obtained. Alternatively, the product having an electrochemical activity, such as hydrogen peroxide, produced during the enzymatic-catalyzing reaction can be detected. The second stage mainly lies in the addition of an electron transporter, which improves the efficiency of the transportation of electrons to the surface of the electrode. Furthermore, the electron transporter has the property of reversing the reduction/oxidation reactions so that it can receive the electrons produced from the enzymatic-catalyzing reaction and become the reduced form, and the oxidation reaction on the surface of the electrode can pass the electrons to the electrode so as to generate electric signals. Because of the low reduction/oxidation potential of the electron transporter, it can decrease the electric potential required for the detection and avoid the interference caused by the substances produced under the high electric potential condition. In the third stage, co-factors of enzymes are applied so as to decrease the resistance resulting from the transportation of electrons from the enzyme during the enzymatic-catalyzing oxidation or reduction reaction. Nicotinamide adenine dinucleotide (NADH) is the commonly used co-factor, and transports electrons to the electrode by way of the reversible oxidation/reduction process. A lot of research has demonstrated that the efficiency of electron transportation of the biosensor used at this stage is far higher than those used in the previous two stages and thus the sensor has a higher sensitivity. However, the disadvantages of the biosensor used at this stage are the complexities on the enzyme immobilization procedure and the poor stability under room temperature, and thus it is not suited for transportation and storage.

Because antibodies/antigens or complementary or partially complementary double-strand ribonucleic acids (RNA) or deoxyribonucleic acids (DNA) are biological molecules having high selectivity and affinity, they can be designed to detect different molecules. Researchers can immobilize the biological molecules having high selectivity and affinity on various types of sensors as the tag for the detection. The biological molecules include, but are not limited to antibodies, antigens, enzymes, nucleic acids, tissues or cells. For example, by the utilization of the mechanism similar to the conventional solid phase immunoassay, a combination of an electrochemical device and a selected and immobilized antibody can be used for the detection of the binding of the solid-phase molecules (e.g., the antibody) with the corresponding mobile-phase molecules (e.g., the antigen). In this combination, a converter in the sensor amplifies the detected electric signals so that a quantitative analysis can be conducted. Such combination is called an "electrochemical immunosensor."

The enzyme-labeled electrochemical immunosensor is the most well-developed system in the art. A non-heterogeneous enzymatic immunoassay comprises two analytic methods, i.e., the competitive analysis and the sandwich analysis. A competitive analysis mainly comprises the steps of: (1) immobilizing an antibody, which is specific to the targeting antigen, on the surface of an electrode; (2) contacting the electrode with an enzyme-labeled targeting antigen and the antigen sample; (3) rinsing the electrode to remove the unbound antigen, (4) adding the substrate for the labeled enzyme to conduct the catalytic reaction and thus produce the electrochemical product; and (5) quantifying the amount of the targeting antigen in the sample by measuring the amount of said product. The electric signal obtained from the competitive analysis is in inverse proportion to the concentration of the targeting antigen. In contrast, the electrical signal obtained from the sandwich analysis is in direct proportion to the concentration of the targeting antigen. Compared to the traditional immunoassay, an electrochemical immunosensor can effectively decrease the operation cost for analyzing various samples presented in a small amount. However, when an electrochemical immunosensor is actually used, it is often found that the electric signal measured cannot be distinguished from the background noise because of the low concentration of the target. Thus, there is a need to develop an electrochemical immunosensor that has a biologically sensory electrode strip capable of amplifying the redox electrical signal and improving the accuracy of the result.

A wide number of species of the biological samples or molecules can be detected by the immunoassay. For example, *Escherichia coli* (*E. coli*) and *Vibrio parahaemolyticus*, which cause food poisoning, are the common research subjects for developing new immunoassays. There are a variety of pathogenic bacteria in a person's daily diet. Traditionally, in order to identify the species of a bacterium precisely, different cultural broths and selective media and further biochemical reaction tests are needed. Therefore, a traditional detecting method is more time-consuming and labor-intensive. Moreover, it cannot detect and identify new strains or mutants of the pathogenic bacteria. It is also a problem that urgently requires a solution.

U.S. Pat. No. 6,491,803, CN 1462880 A and CN 1462881 A pertain to the application of a nano-scaled material to a biochemically sensory electrode. However, these cases still require complicated preparation procedures. For the preparation of the test strip disclosed in U.S. Pat. No. 6,491,803 B1, all reaction substances, including nanometer metal particles, must be first admixed and then coated on the electrode by screen printing, and, in order to evenly coat the admixed substances, the conditions for screen printing are rather strict. In CN 1462880 A and CN 1462881 A, at least three layers of materials including a water-soluble polymer carrier (e.g., carboxymethyl cellulose), a modified nanometer carbon tube and an enzyme reaction layer (including an enzyme, an electron mediator, a stabilizer, a buffer, etc.) are sequentially coated and dried on the test strip. Therefore, the preparation processes disclosed in the two cases are complex. TW Patent No: 1276799 discloses a simplified process for the preparation of a biochemically sensory electrode.

In the combination of all the technologies described above, which include the utilization of the electron mediator, the identification process of the biological materials having affinity to each other, and the utilization of the nanometer materials on electrochemical measurement, an artisan cannot easily deduce the solution to the problems caused by the repetitious soaking and washing procedures conducted in the immuno-identification process, and to the problem of low signal/noise ratio in view of the low concentration of the immunoassay target. Therefore, in this technical field, there is a need to develop a technology to prepare an electrode strip without the complicated preparation processes conventionally used, and to obtain strong electric signals from the electrode strip. The present invention provides an applicable solution for this object.

SUMMARY OF THE INVENTION

One object of the present invention is to provide an electrode strip for measuring an electrochemical signal on which the surface is modified to increase the redox electric signal. The electrode strip comprises:
  an insulating flat substrate;
  an electrode system having a conductive film that is coated on one side of the insulating flat substrate to form a working electrode and a reference electrode that are segregated from each other;
  an insulating layer, coated on the insulating flat substrate, that partially covers the electrode system so that one uncovered portion on the electrode system with the working electrode and the reference electrode becomes a conductive wire connecting end, and another uncovered portion on the electrode system with the working electrode and the reference electrode becomes an electrochemical reaction end;
  a nano-scaled gold particle layer, which covers at least part of the electrochemical reaction end on the working electrode; and
  a lipid-soluble electron mediator layer, which covers at least part of the electrochemical reaction end of the working electrode.

Another object of the present invention is to provide a biosensor comprising the electrode strip of the present invention.

BRIEF DESCRIPTION OF THE DRAWINGS

FIG. 2(A) shows the cross-section of the electrochemical reaction end (5). FIG. 2(B) shows that the electrochemical reaction end (5) is coated with the lipid-soluble electron mediator layer (9). FIG. 2(C) shows that the electrochemical reaction end (5) is coated with the lipid-soluble electron mediator layer (9) and the nano-scaled gold particle layer (7). FIG. 2(D) shows that the electrochemical reaction end (5) is bound with the bridging element (8). FIG. 2(E) shows that the electrochemical reaction end (5) is coated with the lipid-soluble electron mediator layer (9) and bound with the bridging element (8). FIG. 2(F) shows that the electrochemical reaction end (5) is coated with the lipid-soluble electron mediator layer (9) and the nano-scaled gold particle layer (7), and bound with the bridging element (8). FIG. 2(G) shows that the electrochemical reaction end (5) is coated with the nano-scaled gold particle layer (7) and bound with the bridging element (8).

Figure 1:
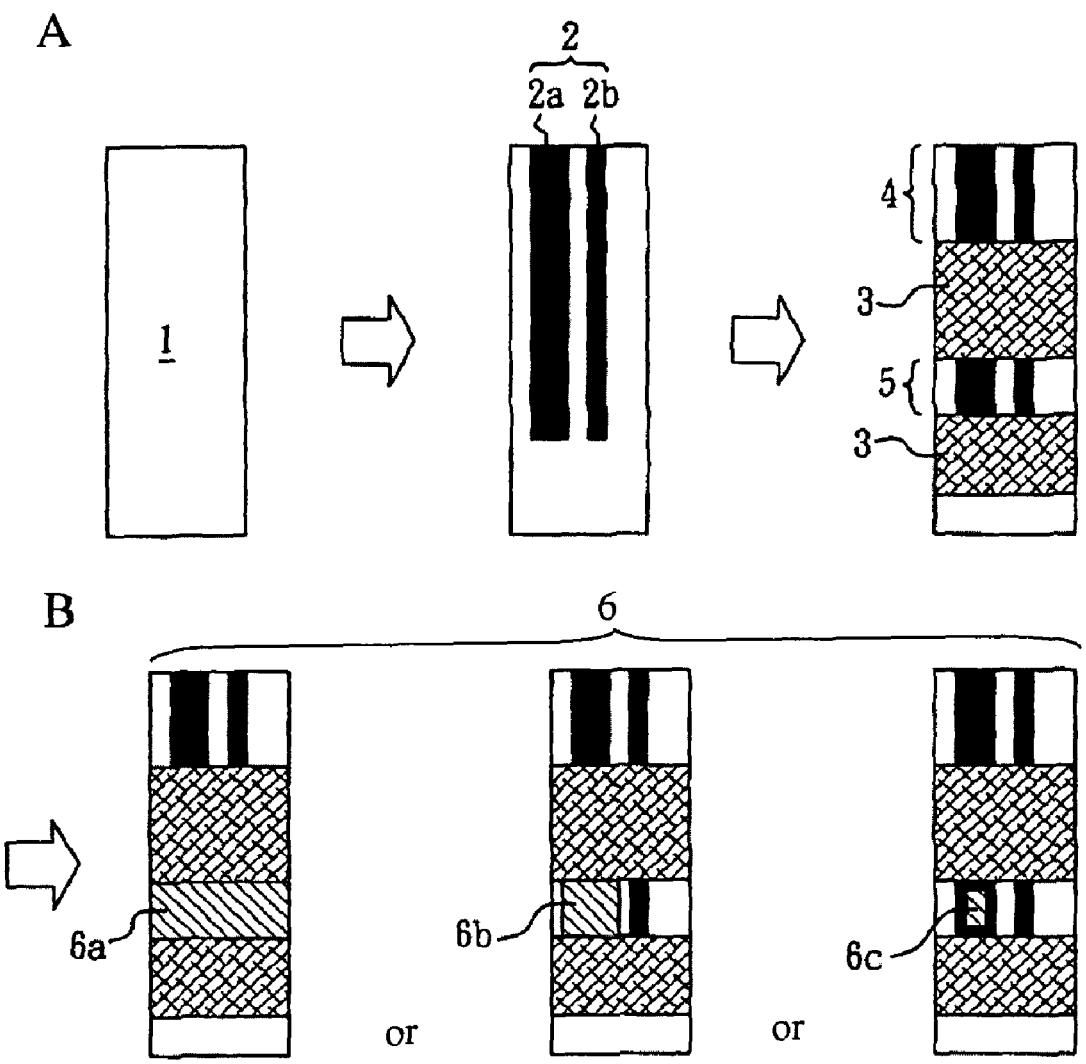
FIG. 1(A) is an exploded schematic view of one embodiment of the preparation and the elements of the electrode strip of the present invention.
FIG. 1(B) shows three embodiments of the coverage of the nano-scaled gold particle layer (7) and the lipid-soluble electron mediator layer (9) on the electrochemical reaction end (5) of the electrode system.

BRIEF DESCRIPTION OF THE REFERENCE NUMERALS SHOWN IN THE DRAWINGS 1 insulating flat substrate
2 electrode system
2*a* working electrode
2*b* reference electrode
3 electrically insulating layer
4 conductive wire connecting end
5 electrochemical reaction end
6 embodiments of the coverage of the modified electrode layer
6*a* completely covered electrochemical reaction end
6*b* completely covered working electrode
6*c* partially covered working electrode
7 nano-scaled gold particle layer
8 bridging element
9 lipid-soluble electron mediator layer
10 the first antibody
11 antigen
12 the second antibody
13 redox enzyme

DEPSCRIPTION OF THE INVENTION

The present invention relates to an electrode strip and the biosensor comprising the same, which is characterized by the fact that a nano-scale gold particle layer (7) and a lipid-soluble electron mediator layer (9) are used to synergistically amplify the electric signal transferred from the redox enzymes (13). Unlike the complicated processing steps required in the prior art, only two layers of materials need to be coated on the electrochemical reaction region of the electrode strip of the present invention. Therefore, the manufacture cost of the electrode strip of the present invention can be reduced, and meanwhile, the electric signal can be amplified.

One object of the present invention is to provide an electrode strip for measuring an electrochemical signal on which the surface is modified to increase the redox electric signal. The electrode strip comprises:
  insulating flat substrate (1);
  electrode system (2) having a conductive film that is coated on one side of the insulating flat substrate (1) to form a working electrode (2*a*) and a reference electrode (2*b*) that are segregated from each other;

an insulating layer (3), coated on the insulating flat substrate, that partially covers the electrode system (2) so that one uncovered portion on the electrode system forms a conductive wire connecting end (4) on the working electrode (2a) and the reference electrode (2b), and another uncovered portion on the electrode system forms an electrochemical reaction end (5) on the working electrode (2a) and the reference electrode (2b);

a nano-scaled gold particle layer (7), which covers at least part of the electrochemical reaction end (5) on the working electrode (2a); and a lipid-soluble electron mediator layer (9), which covers at least part of the electrochemical reaction end (5) of the working electrode (2a).

According to the present invention, the insulating flat substrate (1) has a flat surface and the properties of electrical insulating and thermal resistance under the temperature ranging from 40° C. to 200° C., so that it is suitable for heating processing. Materials suitable for the flat insulating substrate include, but are not limited to, polyvinyl chloride, fiberglass, polyester, bakelite plate, polyethylene terephthalate, polycarbonate, polypropylene, polyethylene, polyamide, polystyrene, glass, and ceramics.

According to the present invention, the conducting film of the electrode system is coated on one side of the insulating flat substrate (1). The conducting film is preferably a reticular printing metal film (i.e., the reticular electrode disclosed in U.S. Pat. No. 6,923,894 B2) or an adhesive metal film (see U.S. Pat. No. 6,254,736 B1). Materials suitable for metal film include, but are not limited to, gold, silver, platinum, and palladium. Suitable printing inks for reticular printing include, but are not limited to, carbon ink, gold ink, silver ink, the mixture of carbon ink and silver ink, volatilizable graphite, copper ink, and any combination thereof, e.g., the silver ink is printed first and then the carbon ink. In one embodiment of the present invention, the reticular electrode comprises a silver ink layer and a carbon ink layer, and the carbon ink layer covers the silver ink layer.

According to the electrode system of the present invention, the area of the working electrode is generally larger than that of the reference electrode.

According to the present invention, the thickness of the insulating layer (3) is about 0.01 mm to 0.6 mm. All the insulating materials known in the field are suitable for the insulating layer of the present invention. The insulating material is coated on the electrode system (2) by means of reticular printing technology. In one embodiment of the present invention, the electrode system (2) has two insulating layers (3) crossing the middle portion and the end portion of the electrode system (2), respectively, so as to divide the electrode system (2) into an electrochemical reaction end (5) and a conductive wire connecting end (4).

According to the present invention, the nano-scaled gold particle layer (7) is made by coating the nano-scaled colloid gold solution on the electrochemical reaction end (5) of the working electrode (2a) and then the gold particle will physically adhere to the surface of the electrochemical reaction end (5). Alternatively, the surface of the electrochemical reaction end (5) can be modified beforehand with a bridging element (8) (see FIGS. 2F and 2G) so that the nano-scaled gold particles can be more evenly fixed on the surface of the electrochemical reaction end (5) and the bridging element (8) can subsequently link to other substances, e.g., a protein, such as an antibody, ligand or receptor, a compound or a nucleotide sequence. The suitable size of the nano-scaled gold particle of the present invention is less than 100 nanometers, preferably about 5 to 50 nanometers, more preferably about 13 nanometers. According to the present invention, the suitable nano-scaled colloid gold solution is the nanometer gold suspension resulting from the reduction of $HAuCl_4$ with a proper catalyst, such as a sodium citrate solution.

According to the present invention, the lipid-soluble electron mediator layer (9) is made by coating a solution, that is obtained from dissolving a lipid-soluble electron mediator in an organic solvent, on the surface of the electrochemical reaction end and then the lipid-soluble electron mediator will physically adhere to the surface of the electrochemical reaction end (5). Therefore, the lipid-soluble electron mediator will not be washed off during the repetitious soaking and washing procedures, and the coating procedure of the present invention avoids the complicated covalent binding procedures for the preparation of the conventional electrode systems. The lipid-soluble electron mediators suitable for the present invention have a reduction/oxidation property for receiving or providing electrons, which include, but are not limited to, tetrathiafulvalene, tetracyanoquinodimethane, meldola blue and ferrocene or the derivatives thereof. Ferrocene or the derivatives thereof are preferably used (Joseph Wang., 2000, Analytical Electrochemistry), and 1,1'-ferrocenedicarboxylic acid is more preferably used. The organic solvents suitable for dissolving the lipid-soluble electron mediator include, but are not limited to, ketones, alcohols and Dimethyl Sulfoxide (DMSO). Ethanol is preferably used.

According to the present invention, there is no limitation to the order for coating the nano-scaled gold particle layer and the lipid-soluble electron mediator layer. The nano-scaled gold particle layer is preferably coated first and then the lipid-soluble electron mediator layer.

According to the present invention, the expression "cover at least part of electrochemical reaction end" refers to the complete coverage of the electrochemical reaction end (5) by the nano-scaled gold particle layer (7) and/or the lipid-soluble electron mediator layer (9) (see FIG. 16a), the complete coverage of the electrochemical reaction end of the working electrode (2a) by the nano-scaled gold particle layer (7) and/or the lipid-soluble electron mediator layer (9) (see FIG. 1B 6b) only, or the partial coverage of electrochemical reaction end of the working electrode (2a) by the nano-scaled gold particle layer (7) and/or the lipid-soluble electron mediator layer (9) (FIG. 1B 6c).

According to the present invention, the surface-modified electrode strip for measuring an electrochemical signal may further comprise a binding element that can specifically bind to the target molecule, and the binding element is linked to the surface of the electrochemical reaction end of the working electrode. Suitable binding elements include, but are not limited to, a protein (such as an antibody, an antigen, a protein ligand or a receptor), a nucleotide sequence and a compound. Persons having ordinary skill in the art can choose the binding element on the basis of the binding characteristic of the target molecule (such as the antibody/antigen or ligand/receptor binding property, or the nucleotide hybridization property), and fix the chosen binding element on the surface of the electrochemical reaction end according to well-known technologies (Electra Gizeli et al., 2001, Biomolecular Sensors). For example, the binding element can be linked with a bridging element (8) fixed on the surface of the electrochemical reaction end. It is known by persons having ordinary skill in the art that the target molecule may be a medical diagnosis marker, a drug, a microorganism, a toxin, an environmental pollutant, or a nucleotide molecule.

The electrode strip, when the binding element specifically binds to the target, can generate an electrochemically active product through the reaction of the redox enzyme (13) with its substrate, and then the amount of the electrochemically active product can be detected so as to quantitatively determine the amount of the target. The redox enzymes (13) suitable for the present invention include, but are not limited to, glucose oxidase, glucose reductase, lactose oxidase, pyruvate oxidase and hydrogen peroxidase. Hydrogen peroxidase is preferably used in electrochemical measurement because it can react with hydrogen peroxidase. According to the present invention, the operation voltage of the combination of hydrogen peroxidase, hydrogen peroxide and lipid-soluble electron mediator is about 150 to 420 mV. According to one embodiment of the present invention, the voltage applied in the electrochemically measuring mode of an ampere-immunosensor for detecting a microbiological antigen is about 300 mV.

Figure 5:
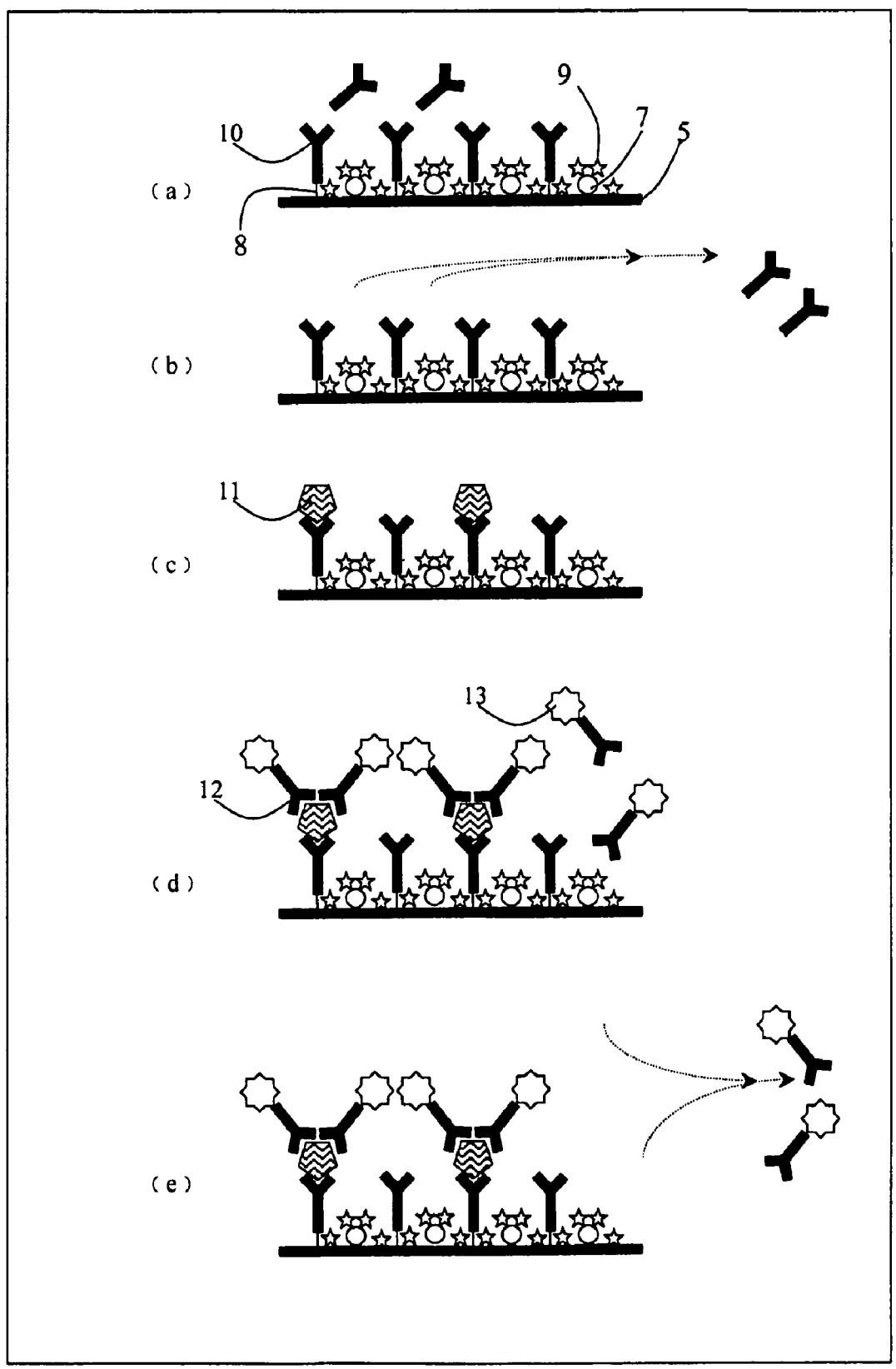
FIGS. 5(*a*) to (*e*) show the scheme described in Example 3 for the immobilization of the redox enzyme.

According to a preferred embodiment of the present invention (as shown in FIG. 5), the binding element is a first antibody (10). The first antibody directly binds to the surface of the electrochemical reaction end (5) through affinity, or links to the bridging element (8) which is covalently bound to the surface of the electrochemical reaction end (5) (as shown in FIG. 5(*a*)). The first antibody specifically binds to the antigen (11) to be measured (as shown in FIG. 5(*c*)), and then the antigen (11) binds to a second antibody (12)-redox enzyme (13) complex (as shown in FIG. 5(*e*)), wherein the second antibody (12) specifically binds to the antigen (11), to form a redox enzyme layer. The redox enzyme layer reacts with hydrogen peroxide and then the electrochemical signal produced is measured.

According to another preferred embodiment of the present invention, the binding element is an antigen (11). The antigen (11) directly binds to the surface of the electrochemical reaction end (5) through affinity, or links to the bridging element (8) which is covalently bound to the surface of the electrochemical reaction end (5). The antigen (11) specifically binds to the first antibody (10) to be measured, and then the first antibody binds to a second antibody (12)-redox enzyme (13) complex, wherein the second antibody (12) specifically binds to the first antibody (10), to form a redox enzyme layer. The redox enzyme layer reacts with hydrogen peroxide and then the electrochemical signal produced is measured.

According to the present invention, the first antibody (10) and the second antibody (12) may be independently a monoclonal or polyclonal antibody. Moreover, the sandwich immuno-recognition biding assay shown in FIG. 5 and the other assays known in the art, such as competitive recognition binding assay, are all applicable to the present invention.

According to the present invention, persons having ordinary skill in the art can choose a proper bridging element (8) on the basis of the species of the binding element (e.g., a protein (such as an antibody, an antigen, a protein ligand or a receptor), a nucleotide sequence or a compound). The bridging elements can evenly spread on the surface of the electrochemical reaction end and form a mono- or multilayer arranged structure. According to the present invention, the bridging element is a compound having two identical or different functional groups, wherein one functional group links to the surface of the electrochemical reaction end (5) and the other links to the binding element. Suitable functional groups on the bridging element include, but are not limited to, carboxyl, thiol, hydroxy, amino, and aldo group. The bridging element is preferably an aldo-containing compound, and, most preferably, is glutaraldehyde.

According to the preferred embodiment of the present invention, the redox enzyme layer is formed by the steps of:
(a) binding the first antibody (10) or the bridging element (8)-first antibody (10) complex to the surface of the electrochemical reaction end (5);
(b) washing off the unbound first antibody (10) or bridging element (8)-first antibody (10) complex;
(c) contacting the electrochemical reaction end (5) with the antigen (11);
(d) contacting the electrochemical reaction end (5) with the second antibody (12)-redox enzyme (13) complex; and
(e) washing off the unbound second antibody (12)-redox enzyme (13) complex.

Alternatively, the steps may be:
(a) binding the first antibody (10) or the bridging element (8)-first antibody (10) complex to the surface of the electrochemical reaction end (5);
(b) contacting the antigen (11) with the second antibody (12)-redox enzyme (13) complex to form an antigen (11)-second antibody (12)-redox enzyme (13) complex;
(c) contacting the first antibody (10) with the antigen (11)-second antibody (12)-redox enzyme (13) complex, or contacting the bridging element (8)-first antibody (10) complex with the antigen (11)-second antibody (12)-redox enzyme (13) complex; and
(d) washing off the unbound antigen (11)-second antibody (12)-redox enzyme (13) complex.

In a further embodiment of the present invention, the steps may be:
(a) binding the antigen (11) or the bridging element (8)-antigen (11) complex to the surface of the electrochemical reaction end (5);
(b) washing off the unbound antigen (11) or bridging element (8)-antigen (11) complex;
(c) contacting the electrochemical reaction end (5) with the first antibody (10);
(d) contacting the electrochemical reaction end (5) with the second antibody (12)-redox enzyme (13) complex; and
(e) washing off the unbound second antibody (12)-redox enzyme (13) complex.

In another embodiment of the present invention, the steps may be:
(a) binding the antigen (11) or the bridging element (8)-antigen (11) complex to the surface of the electrochemical reaction end (5);
(b) contacting the first antibody with the second antibody (12)-redox enzyme (13) complex to form a first antibody (10)-second antibody (12)-redox enzyme (13) complex;
(c) contacting the antigen with the first antibody (10)-second antibody (12)-redox enzyme (13) complex, or contacting the bridging element (8)-antigen (11) complex with the first antibody (10)-second antibody (12)-redox enzyme (13) complex; and
(d) washing off the unbound first antibody (10)-second antibody (12)-redox enzyme (13) complex.

Another objective of the present invention is to provide a biosensor comprising the electrode strip described in the specification and a detecting device. The detecting device is preferably an electric current sensor consisting of a voltage output device, a signal-receiving device and a display device. The voltage output device can provide a voltage of less than 300 mV to the electrochemical reaction region of the electrode strip of the present invention so as to promote the reaction between the reaction layer and the specific target in the sample and then enable the electron mediator to be oxidized from its reduction form to an oxidative form. The signal-receiving device can receive the changes of electric current, voltage or resistance, and transfer the changing signals to the display device so that the amount of the specific target in the sample can be displaced.

The electrode strip of the present invention does not need the complicated procedures for the preparation of the conventional strips, and can amplify the electric signal simultaneously. In addition, the designation of the electrode strip of the present invention can reduce the lowest amount of the sample that can be detected, and has one or more sampling regions (for example, the electrode strip can directly contact the sample or the sample can be dropped on the electrode strip). Therefore, the electrode strip of the present invention not only can be produced easily but also provides an electrode signal sufficient for detection.

The following examples explicate the feasibility of the invention in order to substantiate its technical contents but not to limit the scope. Any variations of and modifications to the invention by persons skilled in the art on the basis of the teaching of the prior art are within the scope of the invention.

EXAMPLE 1

According to the method disclosed in Example 1 of U.S. Pat. No. 6,923,894 B2, a polymer resin carbon slurry comprising polyvinyl chloride and polyurethanes was screen printed on a PVC board substrate (1) to form an electrode system (2) consisting of a working electrode (2a) and a reference electrode (2b). The substrate was dried, and then an electrically insulating layer was deposited on the side of the substrate having the electrode system, and the working electrode (2a) and the reference electrode (2b) were partly exposed to form a conductive wire connecting end (4) and an electrochemical reaction end (5) on each electrode. The electrode strips obtained were dried and designated as Group A (FIG. 2A).

A small amount of 95% ethanol was added to a proper amount of a lipid-soluble electron mediator (1,1'-ferrocene-dicarboxylic acid), and the mixture was sonicated until the lipid-soluble electron mediator was completely dissolved in the ethanol. The solution was dropped on some electrode strips of Group A to modify the electrochemical reaction end (5). The unbound lipid-soluble electron mediator (9) was washed off by water, and the electrode strips obtained were designated as Group B (FIG. 2B).

Figure 2:
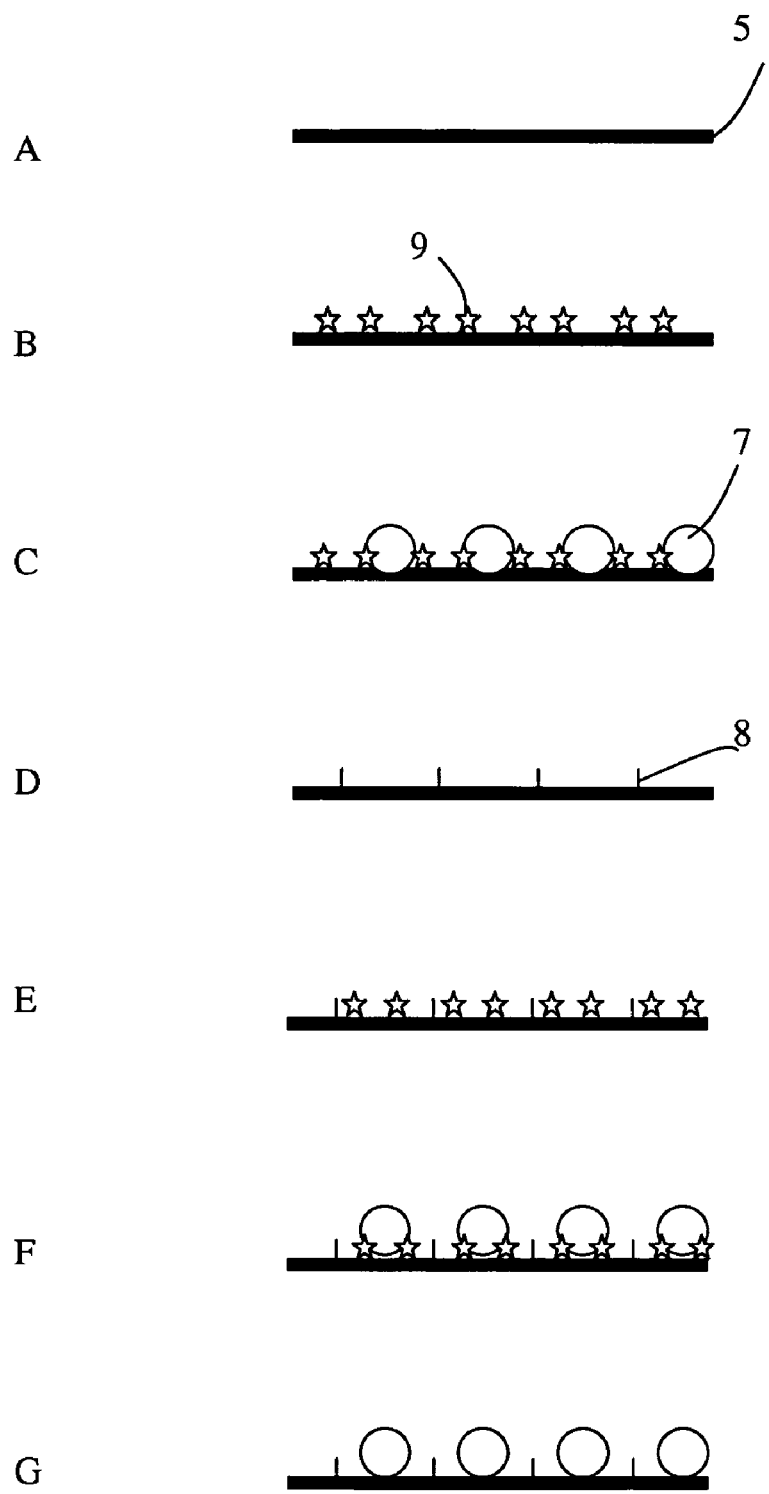
FIG. 2 shows the embodiments of the modified electrode of the present invention.

An HAuCl4 solution (Sigma G-4022) was heated in an oil bath and sodium citrate was added while it was continuously stirred until a wine-red nanometer colloid gold particle solution was obtained. The solution having a gold particle size of about 13 nanometers was dropped on the electrochemical reaction end (5) of the electrode strip of Group A to form a nano-scaled gold particle layer (7). The unbound gold particles and salts were washed off by water. The strip was then coated with a lipid-soluble electron mediator layer (9) as in the process described above. The nano-scaled gold particle layer (7) and lipid-soluble electron mediator layer (9) modified electrode strips were designated as Group C (FIG. 2 C). The optical absorption of the nanometer colloid gold particle solution at 520 nm is about 0.9 to 1.2.

Figure 3:
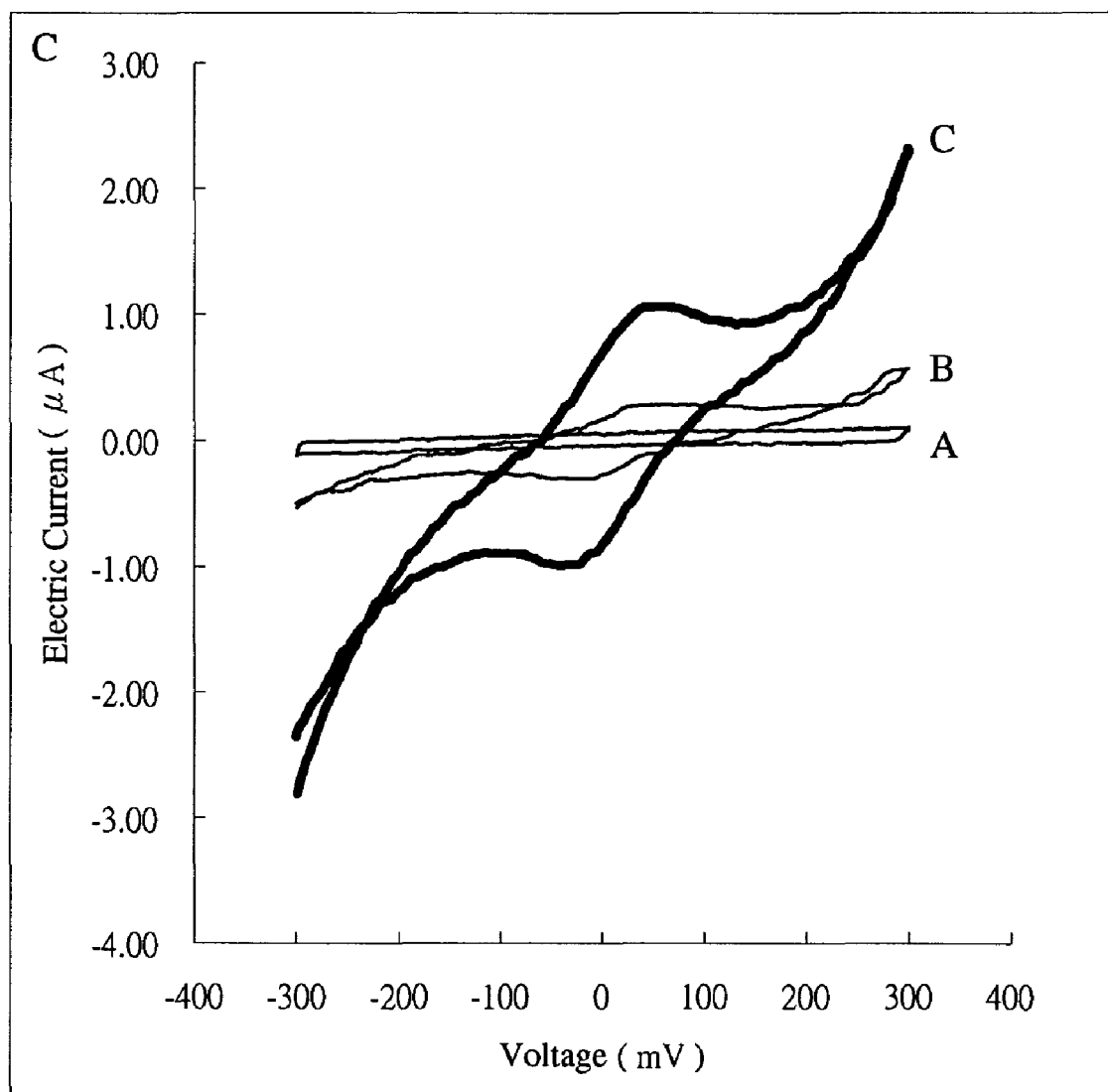
FIG. 3 shows the results of the cyclic voltammetric analysis of Example 1.

In the presence of hydrogen peroxide, the three groups of electrode strips were given a cyclic voltammetric analysis in a phosphate buffer solution of pH 7.2. The peak value of the electric current of Group C was about four times that of group B (FIG. 3). The results prove that the nano-scaled gold particle layer has a property of amplifying the redox electric current on the electrode modified by the lipid-soluble electron mediator.

EXAMPLE 2

Glutaraldehyde (a bridging element (8)) was placed drop by drop on the electrochemical reaction end (5) of the electrode strip of Group A from Example 1. The unbound bridging element (8) was washed off with water, and the obtained electrode strips were designated as Group D (FIG. 2D).

The ethanol dissolved lipid-soluble electron mediator (1,1'-ferrocenedicarboxylic acid) prepared by the method described in Example 1 was placed drop by drop on the electrode strip of Group D to modify its electrochemical reaction end (5). After the unbound lipid-soluble electron mediators were washed off with water, the obtained electrode strips containing the lipid-soluble electron mediator layer (9) were designated as Group E (FIG. 2E).

According to the method described in Example 1, the nanometer colloid gold particle solution having a gold particle size of about 13 nanometers was placed drop by drop on the electrochemical reaction end (5) of the electrode strip of Group D to form a nano-scaled gold particle layer (7). The unbound gold particles and salts were washed off by water. The strip was then coated with the lipid-soluble electron mediator layer (9) as in the process described above. The nano-scaled gold particle layer (7) and lipid-soluble electron mediator layer (9) modified electrode strips were designated as Group F (FIG. 2F).

Figure 4:
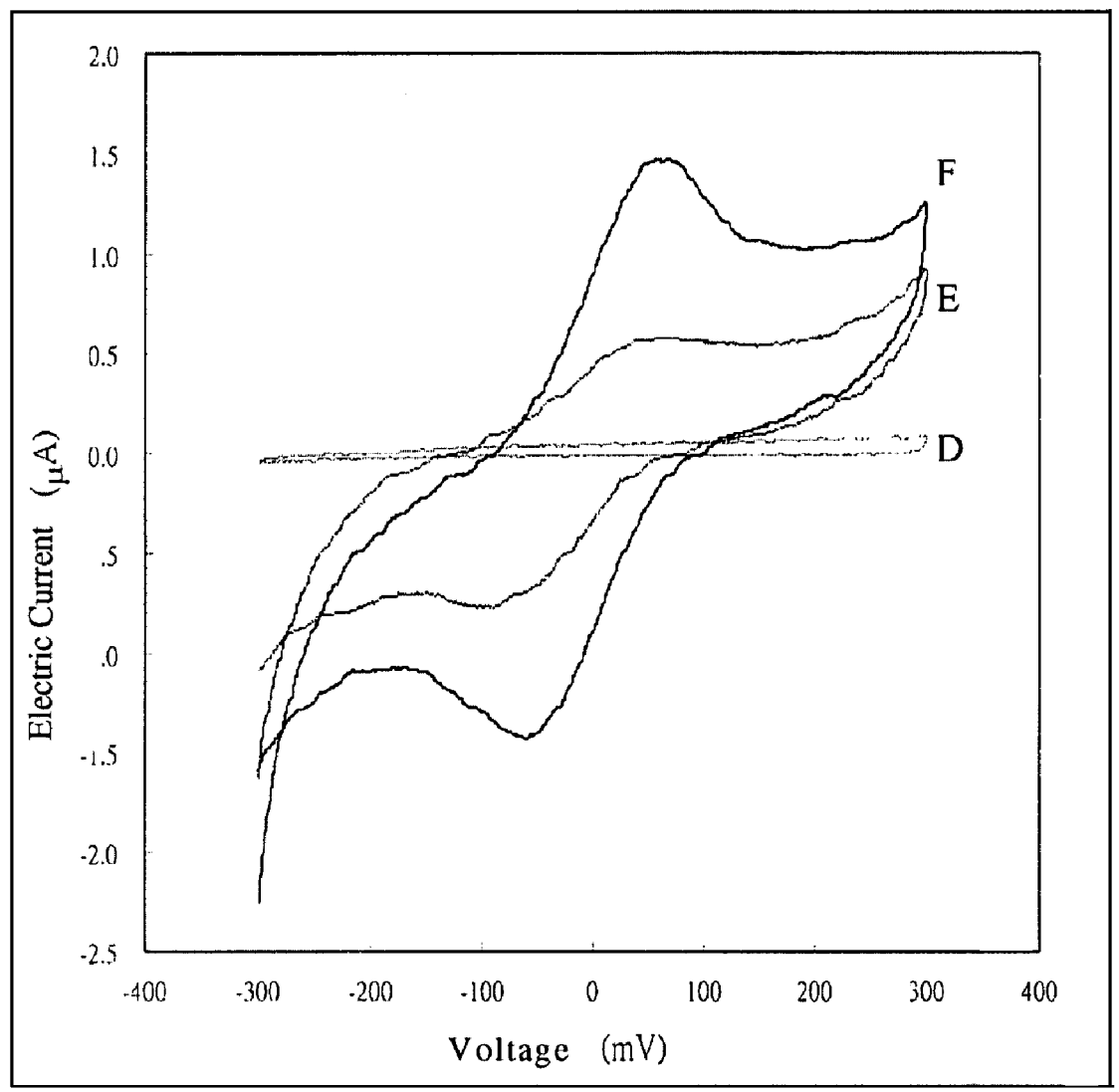
FIG. 4 shows the results of the cyclic voltammetric analysis of Example 2.

The electrode strips of Group D, E and F were tested by cyclic voltametric analysis with the conditions described in Example 1. It was found that the peak value of the electric current obtained from Group F was about three times that of group E (FIG. 4). The results prove that the nano-scaled gold particle layer (7) has a property of amplifying the redox electric current on the electrode modified by the lipid-soluble electron mediator.

EXAMPLE 3

In this test, an antigen (11) in the biological sample was determined. The electrode strip modified by the nano-scaled gold particle layer (7) and the lipid-soluble electron mediator layer (9) was prepared on the basis of the materials and methods for the preparation of Group F described in Example 2. An anti-E. coli O157:H7 monoclonal antibody was used as the first antibody (10). An anti-E. coli O157:H7 polyclonal antibody was used as the second antibody (12) and linked to hydrogen peroxidase to form an anti-E. coli O157:H7 polyclonal-hydrogen peroxidase complex. The hydrogen peroxidase was immobilized on the electrode through the following steps (FIG. 5):
 (a) binding the bridging element (8)-first antibody (10) complex to the surface of the electrode;
 (b) washing off the unbound bridging element (8)-first antibody (10) complex;
 (c) contacting the electrode with the antigen (11);
 (d) contacting the electrode with the second antibody (12)-hydrogen peroxidase complex; and
 (e) washing off the unbound second antibody (12)-hydrogen peroxidase complex.

Figure 6:
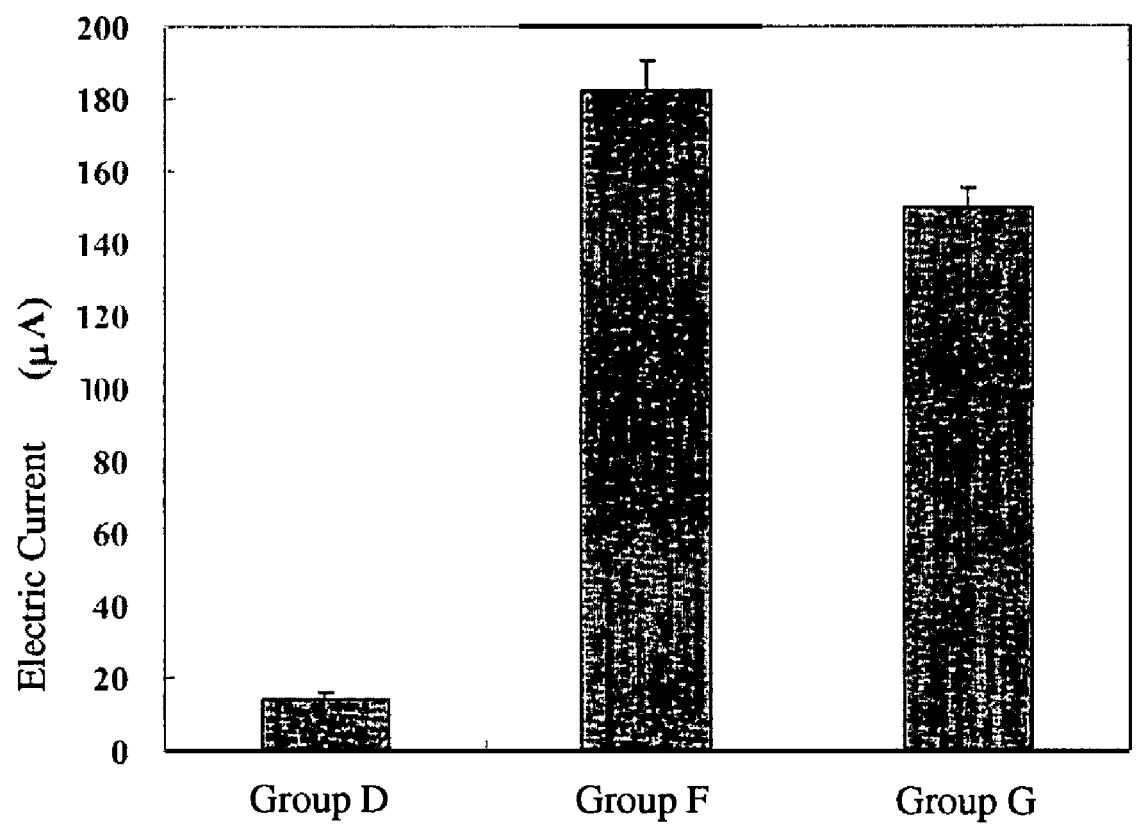
FIG. 6 shows the results of the ampere-immunoassay of Example 3.

The hydrogen peroxide in a phosphate buffer of pH 7.2 was used as the substrate of hydrogen peroxidase. The amount of the microbiological antigen was detected by the electrochemically measuring mode of an ampere-immnosensor at a fixed voltage of 300 mV. Meanwhile, the electrode strip of Group G, which was only modified with the nano-scaled gold particle layer (7) (FIG. 2G), and the electrode strip of Group D of Example 2 were also treated with the same enzymatic immobilization procedures and their immuno-sensitivity to the microorganism was measured as control. The results prove that the lipid-soluble electron mediator layer (9) can further amplify the redox electric current of the electrode modified by the nano-scaled gold particle (FIG. 6).

On the basis of the results described above, it is found that the electrode strip of the present invention, which is modified by the nano-scaled gold particle layer (7) and the lipid-soluble electron mediator layer (9), can synergistically amplify the redox electric current signal. In addition, the lipid-soluble electron mediators disposed on the surface of the composite electrode will not lose their activity even if repetitively soaked and washed. Furthermore, the complex covalent bonding steps are not required for practicing the electrode strip of the present invention. Therefore, the strip of the present invention has the advantages of reducing preparation procedures and decreasing preparation costs. For the relevant electrochemical equipment manufacturing factories that wish to manufacture a strip of good quality and at a low cost, the electrode strip of the present invention modified by the nano-scaled gold particle layer (7) and the lipid-soluble electron mediator layer (9) indeed provides an effective solution.

What is claimed is:

1. A surface-modified electrode strip for measuring electrochemical signals, comprising:
an insulating flat substrate;
an electrode system having a conductive film that is coated on one side of the insulating flat substrate to form a working electrode and a reference electrode that are segregated from each other;
an insulating layer, coated on the insulating flat substrate, that partially covers the electrode system so that one uncovered portion on the electrode system with the working electrode and the reference electrode becomes a conductive wire connecting end, and another uncovered portion on the electrode system with the working electrode and the reference electrode becomes an electrochemical reaction end;
a nano-scaled gold particle layer, which covers at least part of the electrochemical reaction end on the working electrode; and
a lipid-soluble electron mediator layer, which covers at least part of the electrochemical reaction end of the working electrode,
wherein said electrochemical reaction end of the working electrode further comprises a bridging element.

2. The electrode strip of claim 1, wherein the size of the gold particle of the nano-scaled gold particle layer is less than 100 nanometers.

3. The electrode strip of claim 2, wherein the size of the gold particle of the nano-scaled gold particle layer is about 5 to 50 nanometers.

4. The electrode strip of claim 3, wherein the size of the gold particle of the nano-scaled gold particle layer is about 13 nanometers.

5. The electrode strip of claim 1, wherein the nano-scaled gold particle layer completely covers the electrochemical reaction end.

6. The electrode strip of claim 1, wherein the nano-scaled gold particle layer completely covers the electrochemical reaction end of the working electrode.

7. The electrode strip of claim 1, wherein the nano-scaled gold particle layer partially covers the electrochemical reaction end of the working electrode.

8. The electrode strip of claim 1, wherein the lipid-soluble electron mediator of the lipid-soluble electron mediator layer is selected from the group consisting of tetrathiafulvalene, tetracyanoquinodimethane, meldola blue and ferrocene or the derivatives thereof.

9. The electrode strip of claim 8, wherein the lipid-soluble electron mediator is ferrocene or a ferrocene derivative.

10. The electrode strip of claim 9, wherein the ferrocene derivative is 1,1'-ferrocenedicarboxylic acid.

11. The electrode strip of claim 1, wherein the lipid-soluble electron mediator layer completely covers the electrochemical reaction end.

12. The electrode strip of claim 1, wherein the lipid-soluble electron mediator layer completely covers the electrochemical reaction end of the working electrode.

13. The electrode strip of claim 1, wherein the lipid-soluble electron mediator layer partially covers the electrochemical reaction end of the working electrode.

14. The electrode strip of claim 1, wherein the bridging element has two functional groups, and the functional group is selected from the group consisting of carboxyl, thiol, hydroxy, amino, and aldo group.

15. The electrode strip of claim 14, wherein the bridging element is an aldo-containing compound.

16. The electrode strip of claim 15, wherein the bridging element is glutaraldehyde.

17. The electrode strip of claim 1, wherein the electrochemical reaction end of the working electrode further comprises a binding element specifically binding to a target to form a complex.

18. The electrode strip of claim 17, wherein the binding element is a protein, a nucleic acid sequence or a compound.

19. The electrode strip of claim 18, wherein the protein is an antibody, an antigen, a protein ligand, or a receptor.

20. The electrode strip of claim 17, wherein the binding element binds to the electrochemical reaction end of the working electrode through a bridging element.

21. The electrode strip of claim 17, wherein the binding element-target complex and a redox enzyme form a redox enzyme layer.

22. The electrode strip of claim 21, wherein the redox enzyme is selected from the group consisting of glucose oxidase, glucose reductase, lactose oxidase, pyruvate oxidase and hydrogen peroxidase.

23. The electrode strip of claim 21, wherein the redox enzyme layer comprises a first antibody as the binding element, an antigen target and a second antibody-redox enzyme complex that binds to the antigen.

24. The electrode strip of claim 21, wherein the redox enzyme layer comprises an antigen as the binding element, a first antibody that binds to the antigen and a second antibody-redox enzyme complex that binds to the first antibody.

25. A biosensor comprising the electrode strip of claim 1 and the detecting device.

26. The biosensor of claim 25, wherein the detecting device is an electric current sensor consisting of a voltage output device, a signal-receiving device and a display device.

* * * * *